United States Patent

Powers, Jr.

Patent Number: 5,868,701
Date of Patent: Feb. 9, 1999

[54] MEDICAL SUCTIONING BACTERIA VALVE AND RELATED METHOD

[76] Inventor: Carleton A. Powers, Jr., 2268 68th St., SE., Caledonia, Mich. 49316

[21] Appl. No.: 959,849

[22] Filed: Oct. 29, 1997

Related U.S. Application Data

[62] Division of Ser. No. 618,524, Mar. 19, 1996, Pat. No. 5,728,078.

[51] Int. Cl.⁶ .............................. A61M 31/00; A61M 1/00
[52] U.S. Cl. .................................................. 604/49; 604/28
[58] Field of Search .................................. 604/48, 49, 54, 604/30, 245–247, 264–266, 268, 280, 313, 315, 316, 322, 323, 335, 350, 902, 28; 128/898

[56] References Cited

U.S. PATENT DOCUMENTS

| | | |
|---|---|---|
| 1,201,964 | 10/1916 | Howard . |
| 2,187,662 | 1/1940 | Pigott . |
| 2,274,893 | 3/1942 | Freedman . |
| 3,332,422 | 7/1967 | Jinkens et al. . |
| 3,476,144 | 11/1969 | Krantz . |
| 3,482,313 | 12/1969 | Stram . |
| 3,863,635 | 2/1975 | Swatman . |
| 3,906,935 | 9/1975 | Raia et al. . |
| 4,022,218 | 5/1977 | Riddick . |
| 4,083,115 | 4/1978 | McKelvey . |
| 4,083,706 | 4/1978 | Wiley . |
| 4,232,677 | 11/1980 | Leibinsohn . |
| 4,421,123 | 12/1983 | Percarpio . |
| 4,586,900 | 5/1986 | Hymanson et al. . |
| 4,589,869 | 5/1986 | Wernborg . |
| 4,678,459 | 7/1987 | Onik et al. . |
| 4,693,712 | 9/1987 | Bates . |
| 4,712,583 | 12/1987 | Pelmulder et al. . |
| 4,759,752 | 7/1988 | Stober . |
| 4,795,437 | 1/1989 | Schulte et al. . |
| 4,858,619 | 8/1989 | Toth . |
| 4,865,545 | 9/1989 | La Rocca . |
| 4,886,492 | 12/1989 | Brooke . |
| 4,919,167 | 4/1990 | Manska . |
| 5,078,603 | 1/1992 | Cohen . |
| 5,269,769 | 12/1993 | Dhara et al. . |
| 5,464,397 | 11/1995 | Powers, Jr. . |

FOREIGN PATENT DOCUMENTS

| | | |
|---|---|---|
| 445091 | 4/1991 | European Pat. Off. . |
| 2516999 | 10/1976 | Germany . |
| 3316397 | 1/1985 | Germany . |
| 4102182 | 7/1992 | Germany . |
| 394252 | 6/1933 | United Kingdom . |

OTHER PUBLICATIONS

Exhibit A is literature published by SurgiMark Inc. of Yakima, Washington regarding medical yankuer tips. (acknowledged as prior art).

*Primary Examiner*—Wynn Wood Coggins
*Assistant Examiner*—Jennifer R. Sadula
*Attorney, Agent, or Firm*—Warner Norcross & Judd LLP

[57] ABSTRACT

A valve and method for preventing backflow of bacteria and other unhealthy substances in a medical suctioning apparatus. The valve defines a chamber and has an outlet and an opposed inlet. The valve provides a tortuous path that effectively limits backflow of bacteria and other unhealthy substances. The valve further includes a diffuser proximate the outlet to direct backflowing fluids to travel the full length of the tortuous path. The valve is used between a medical suctioning unit and a patient-contacting part such as an ejector, evacuator, or yankauer.

7 Claims, 5 Drawing Sheets

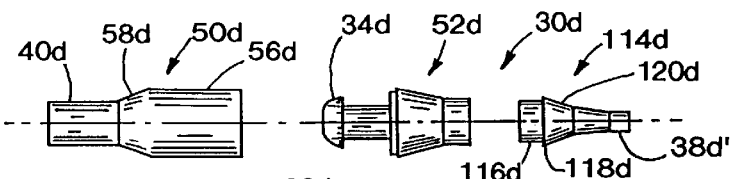
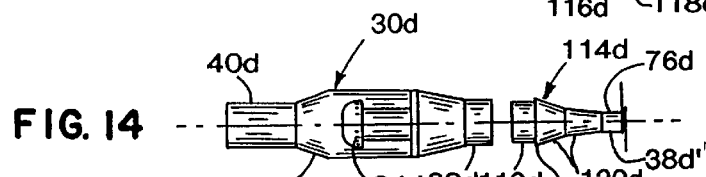
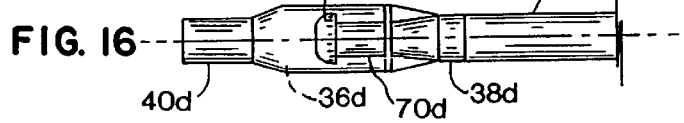
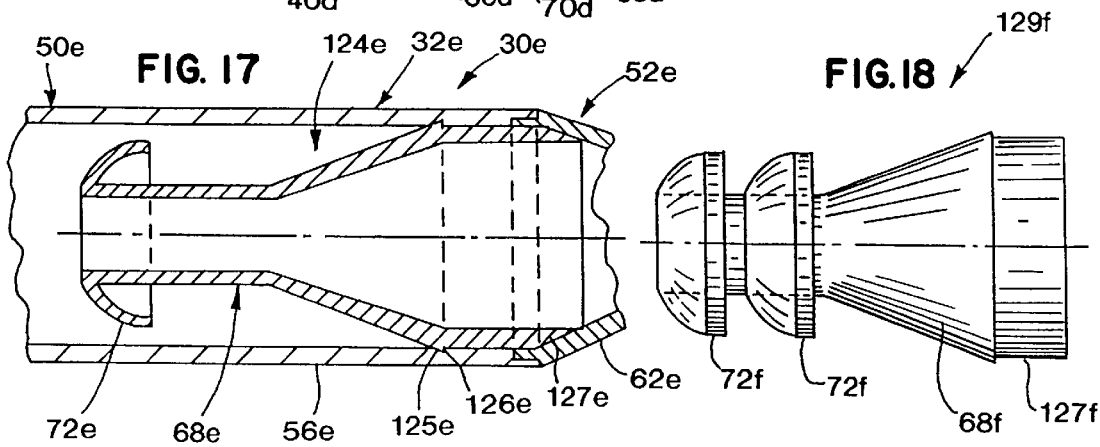
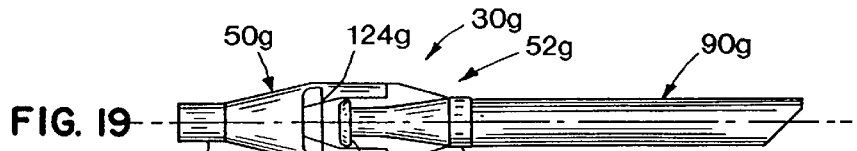
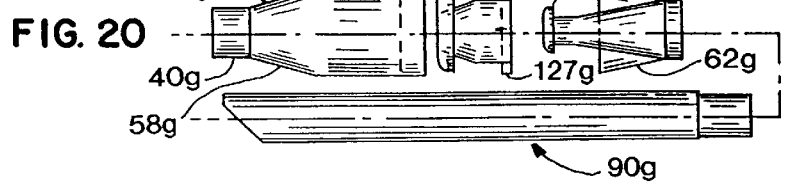

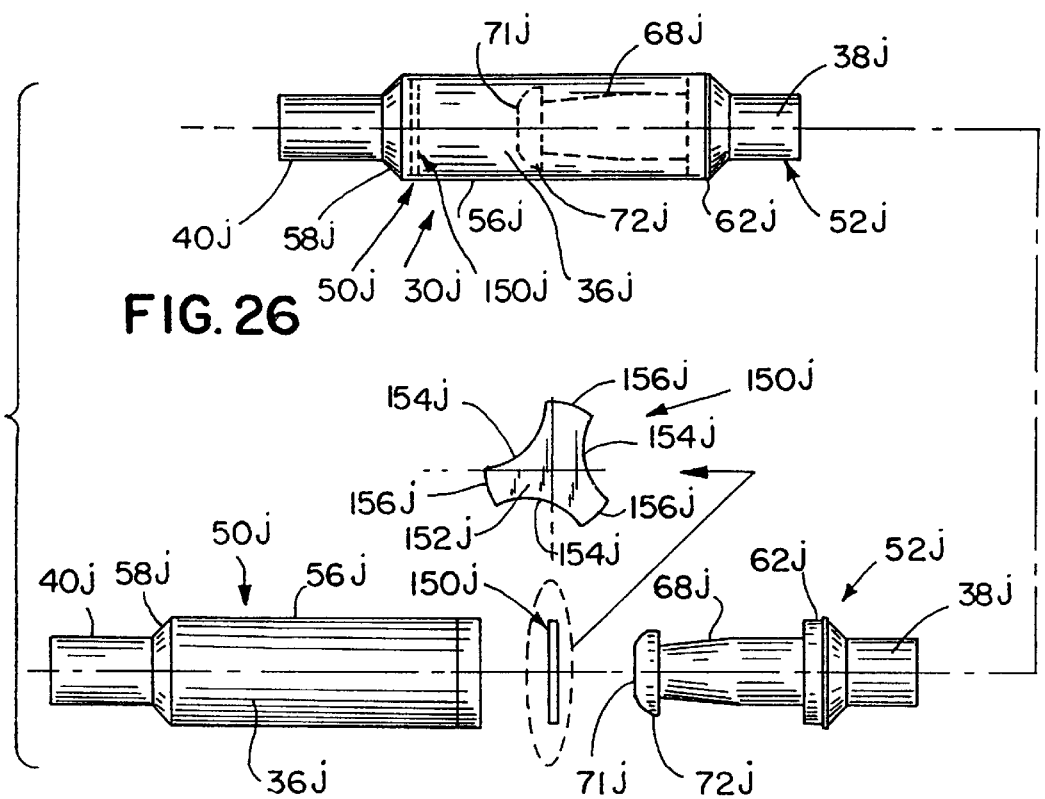

MEDICAL SUCTIONING BACTERIA VALVE AND RELATED METHOD

This is a divisional of application Ser. No. 08/618,524, filed Mar. 19, 1996 now U.S. Pat. No. 5,728,078.

BACKGROUND OF THE INVENTION

The present invention relates to a valve and method for preventing the backflow of body fluids and bacteria through medical suctioning equipment.

Medical centers, hospitals, dental practices, and other medical operations commonly use suctioning equipment to remove body fluids, such as saliva or blood, during medical procedures. These body fluids can carry or become contaminated with bacteria and other unhealthy substances. Consequently, it is important to prevent the body fluids, bacteria, and other unhealthy substances from backflowing or moving in a reverse direction into any patient. This can be problematic since substances such as bacteria will travel along surfaces without the assistance of a fluid carrier. For example, even if the part of the medical suctioning apparatus that contacts a patient is replaced with each new patient, bacteria can travel in a reverse direction through the new part and thus still cause a problem. Therefore, particularly in view of public concern over communicable diseases and diseases that can be transmitted by body fluids, it is important that maximum protection against undesired backflow and/or movement of bacteria be provided.

U.S. Pat. No. 4,083,706 to Wiley discloses a sterile trap accessory inserted between a suctioning conduit and an aspirator. The trap accessory includes a filter for catching debris and a tubular section that protrudes into the trap toward the filter. The filter effectively captures debris for later viewing by a medical worker or doctor; however in doing so large amounts of debris are held in the trap accessory, thus potentially increasing the risk of bacteria movement in a reverse direction. Further, the surfaces between the filter and the inlet to the trap accessory permit backflow of bacteria.

SUMMARY OF THE INVENTION

The aforementioned problems are overcome in the apparatus of the present invention wherein a backflow valve includes a tortuous surface path through the valve that all fluids and bacteria must follow in attempting to move between the outlet and the inlet. Further, all fluids that backflow through the outlet are forced by diffusion or deflection to follow the full tortuous path.

In the associated method, fluid and bacteria backflow is prevented by inserting into the section line a backflow to valve provide a tortuous surface path between the valve outlet and valve inlet. As disclosed, the valve includes a peripheral wall forming a portion of the tortuous path; and the method includes the step of diffusing or directing backflowing liquid toward the peripheral wall so that it must follow the full length of the path.

Fluids are suctioned through the valve from the inlet to the outlet, by drawing a vacuum through the valve but bacteria cannot readily backflow through the valve due to the tortuous path and the diffusion of any backflowing fluid.

These and other objects, advantages, and features of the present invention will be more readily appreciated and further understood by reference to the detailed description of the embodiment and the drawings.

BRIEF DESCRIPTION OF THE DRAWINGS

FIG. 13 is an exploded view of a fifth embodiment valve including an adaptor for converting the valve for use with either an ejector or an evacuator;

FIG. 14 is a partially exploded side view of the valve shown in FIG. 13, the adapter tip being shown as exploded away but as being ready for attachment to the valve;

FIG. 15 is a side view of the assembly shown in FIG. 13;

FIG. 16 is a side view of the valve shown in FIG. 13 connected to an evacuator, the adapter tip having been removed;

FIG. 17 is a fragmentary sectional view of a sixth embodiment valve including an insert including a ring-shaped fin;

FIG. 18 is a side view of an insert for a seventh embodiment valve including a pair of ring-shaped fins;

FIG. 19 is a side view of an eighth embodiment valve connected to a disposable oral evacuator;

FIG. 20 is an exploded side view of the assembly shown in FIG. 19;

FIG. 26 is a side view of an eleventh embodiment valve; and

FIG. 27 is an exploded side view of the valve shown in FIG. 26.

DETAILED DESCRIPTION OF THE PREFERRED EMBODIMENT

Figure 1:
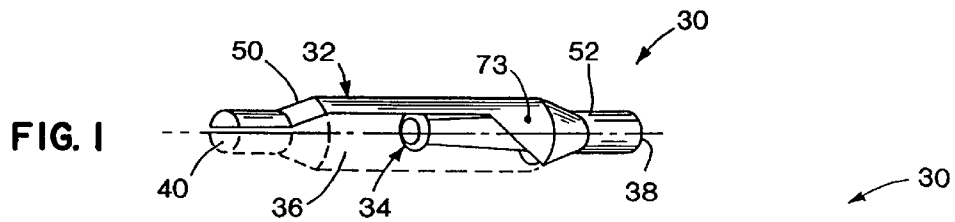
FIG. 1 is perspective view of a first embodiment antibacterial valve with the outer housing partially broken away to illustrate the interior.
Figure 2:
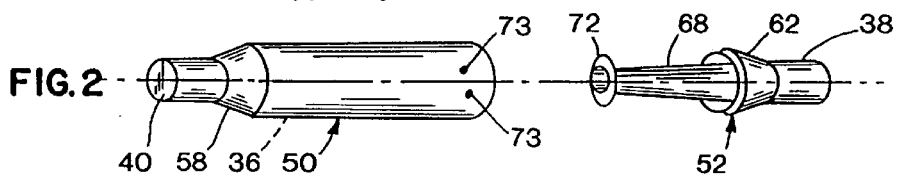
FIG. 2 is an exploded perspective view of the valve.
Figure 3:
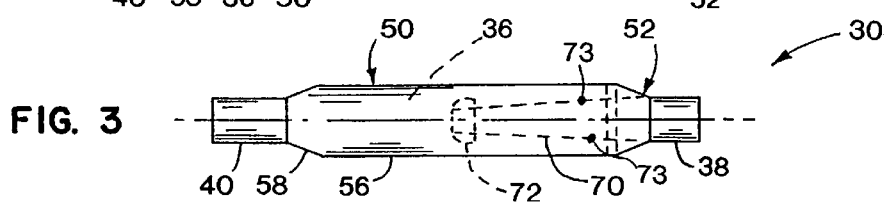
FIG. 3 is a side view of the valve.
Figure 4:
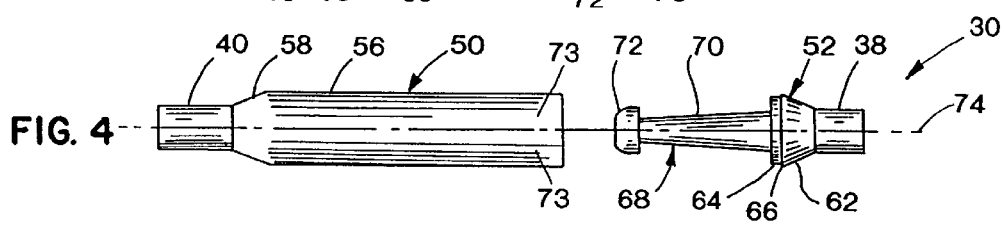
FIG. 4 is an exploded side view of the valve.

An antibacterial valve 30 (FIGS. 1–4) embodying the present invention includes a casing 32 and a tortuous-path-forming member 34 located in casing 32. Casing 32 includes inner surfaces defining a chamber 36, and an inlet 38 and an outlet 40 located at opposite ends of chamber 36. Valve 30 is particularly constructed to allow flow of body fluids through valve 30 from inlet 38 to outlet 40, but is constructed to provide a tortuous path 42 (FIG. 5) to inhibit undesired movement and/or backflow of bacteria and other unhealthy substances from outlet 40 to inlet 38. The "tortuous path" method of preventing backflow of bacteria is based on Pasteur's theory of curved paths for protection from germs. It is contemplated that these valves can be made from disposable or autoclavable materials such as polymeric materials.

Valve 30 (FIG. 4) is a two-piece assembly including a first member 50 and a second member 52 configured to be press fit to first member 50 to frictionally engage and form a leak-free joint with first member 50. First member 50 is tubular and includes the outlet 40, a cylindrically shaped wall 56 of larger diameter than outlet 40, and a frustoconically shaped section 58 connecting outlet 40 and cylindrically shaped wall 56. Second member 52 includes the inlet 38 and a frustoconically shaped section 62 extending from inlet 38. The edge of frustoconically shaped section 62 is configured to matably engage the end of cylindrically shaped wall 56. In particular, the end of frustoconically shaped section 62 includes a ring 64 configured to press-fittingly engage the inside of the end of cylindrically shaped wall 56, and further includes an abutting ring 66 configured to engage the end of cylindrically shaped wall 56 to prevent over-insertion of second member 52 into first member 50. Second member 52 further includes a tubular protruding section 68 that extends from inlet 38 into chamber 36. Tubular protruding section 68 includes an inwardly tapered elongated wall section 70 having a reversely oriented ring-shaped fin 72 on its end that protrudes radially into chamber 36. Ring-shaped fin 72 is preferably oriented at an acute angle to longitudinal centerline 74 and is reversely formed and arcuately shaped so that it extends backwardly toward inlet 38, although it is noted that the angle and shape of ring-shaped fin 72 can be varied for optimal results in specific applications.

Figure 5:
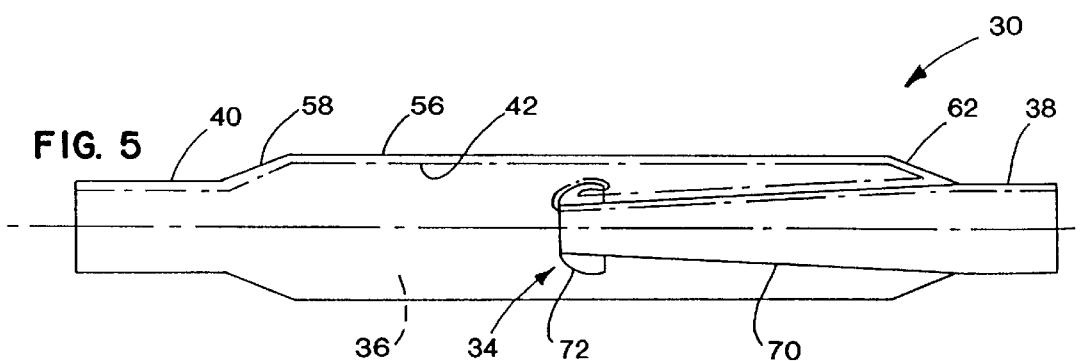
FIG. 5 is an enlarged schematic illustration of the valve showing the tortuous surface path which prevents backflow of bacteria through the valve.

When first and second members 50 and 52 are assembled, casing 32 is defined by cylindrically shaped wall 56, frustoconically shaped section 58, and frustoconically shaped section 62. Tortuous path forming member 34 is defined by tubular protruding section 68 including fin 72. As shown in FIG. 5, the inner surfaces of casing 36 and the surfaces of elongated wall section 70 and fin 72 advantageously form tortuous path 42. The tortuous path 42 prevents undesired movement of bacteria in a counterflow direction through valve 30 in large part because bacteria tends to grow or move along surfaces, or tends to otherwise move in linear paths when moving without the assistance of a flowing carrier fluid.

As illustrated in FIGS. 1–4, vacuum release vents 73 extend through the first member 50 proximate the end opposite the outlet 40. Each vent is "pin size," meaning that it is large enough to permit air to flow in but not large enough to permit liquid, such as saliva or other body fluids to flow out. In the presently preferred embodiment, four such vents 73 are spaced equidistantly around the circumference of the member 50. The vents 73 prevent liquids from becoming entrapped or stagnant with the space surrounding the protruding section 68. Air flowing into the valve 30 through the vents 73 enables fluids to travel along the tortuous path 42 toward the outlet 40.

Advantageously, an antibacterial valve such as valve 30 can be used with a variety of different medical suctioning devices. Further, the valve can be formed in different sizes, shapes and configurations to optimize flow-through characteristics and to facilitate assembly of the valve. The following discussion discloses a variety of valve configurations. To reduce repetitive discussion, comparable items and features in the following discussion are labeled with identical numbers used for valve 30, but with the addition of letters "a," "b," "c," and so forth.

Figure 6:
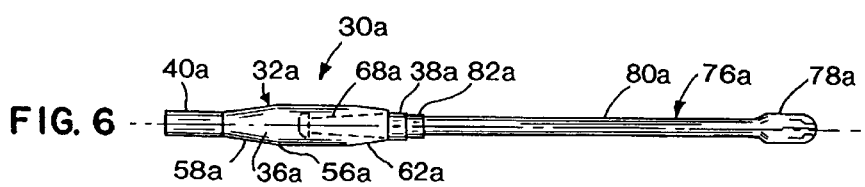
FIG. 6 is a side view of an assembly including a second embodiment valve releasably connected to a saliva ejector.
Figure 7:
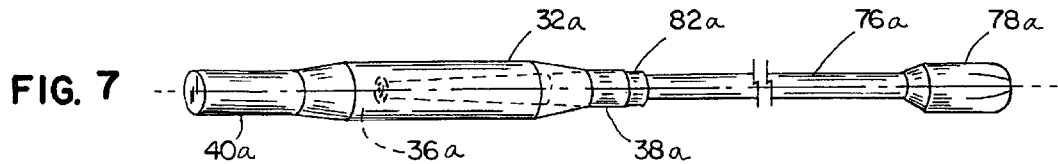
FIG. 7 is a perspective of view of the assembly shown in FIG. 6.
Figure 8:
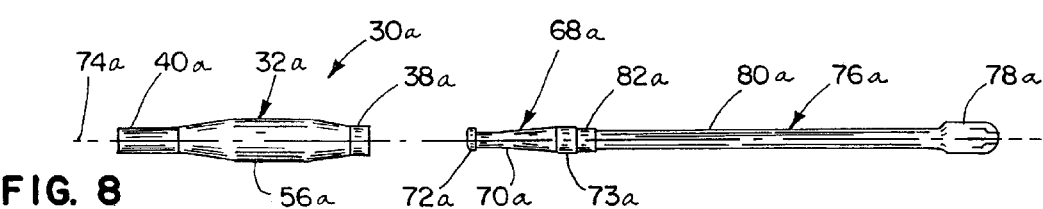
FIG. 8 is an exploded side view of the assembly shown in FIG. 6.

In FIGS. 6 and 7, a valve 30a is shown attached to an ejector 76a such as is commonly used to remove saliva from a patient's mouth. Ejector 76a includes a slotted ejector tip 78a, an elongated deformable tubular straw 80a, and a releasably engageable connector 82a configured to telescopingly and frictionally engage inlet 38a on valve 30a. FIG. 8 shows casing 32a exploded away from ejector 76a, but aligned for connection thereto. Valve 30a includes a one-piece casing 32a having an enlarged mid-section 56a, an inlet 38a, and an outlet 40a. Frustoconically shaped sections 58a and 62a connect inlet 38a and outlet 40a to mid-section 56a, respectively. A tubular second piece or insert 68a is attached to and extends from connector 82a of ejector 76a. Insert 68a includes an elongated wall section 70a including a bulbous section 73a for scalingly engaging the inside of inlet 38a. Bulbous section 73a further has a diameter chosen to scalingly engage the outside of connector 82a. A ring-shaped fin 72a is located on the end of elongated wall section 70a. Ring-shaped fin 72a is configured to telescope into chamber 36a through inlet 38a. A tortuous path is thus defined along the inner surfaces of valve 30a, which tortuous path prevents backflow of bacteria. It is noted that casing 32a is a one-piece molding made, for example, by blow molding or roto-molding. However, casing 32a could also be constructed from a pair of injection molded opposing halves (not specifically shown) which mate along a plane that extends parallel and through centerline 74a of chamber 36a.

Figure 9:
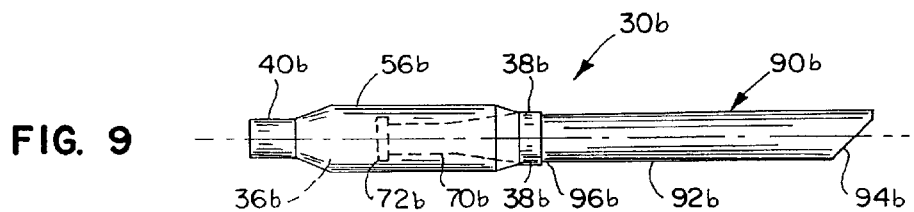
FIG. 9 is a side view of a third embodiment valve releasably connected to a disposable oral evacuator.
Figure 10:
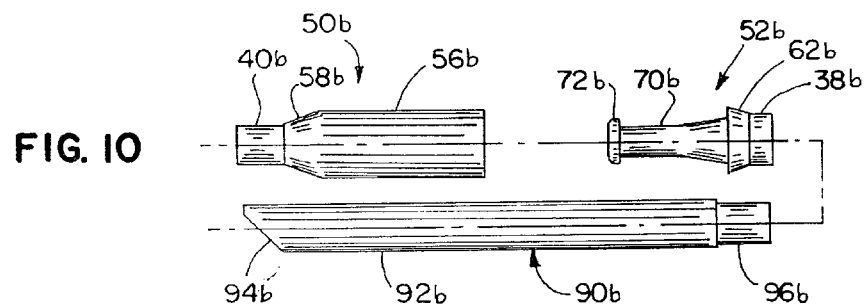
FIG. 10 is an exploded side view of the assembly shown in FIG. 9.

In FIGS. 9 and 10, a valve 30b is shown attached to an evacuator 90b. Evacuators 90b are commonly used in dentistry practice to selectively remove saliva from a patient's mouth. Evacuator 90b has a larger diameter than an ejector such as ejector 76a to facilitate grasping of the evacuator 90b. Evacuator 90b includes a tubular straw 92b including an angled suction end 94b. Straw 92b includes a second end 96b configured to telescopingly press-fittingly engage the inside of inlet 38b. Alternatively, it is contemplated that evacuator end 96b could engage an outside of inlet 38b. Notably, valve 30b includes members 50b and 52b that are comparable to members 50 and 52 of valve 30, although members 50b and 52b have different proportions as needed for optimal flow-through characteristics when connected to evacuator end 96b.

Figure 11:
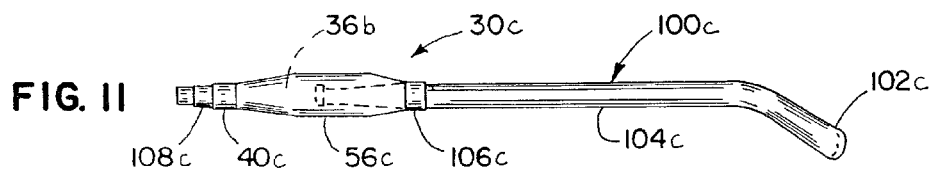
FIG. 11 is a side view of a fourth embodiment valve releasably connected to a disposable medical suction yankauer.
Figure 12:
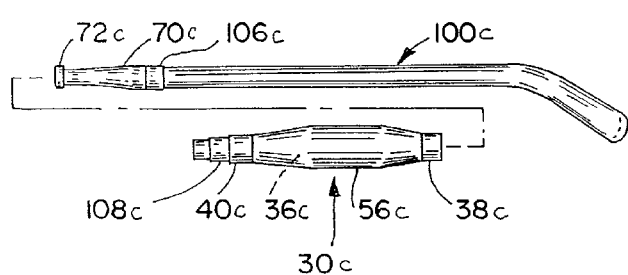
FIG. 12 is an exploded side view of the assembly shown in FIG. 11.

FIGS. 11 and 12 show a valve 30c attached to a yankauer 100c. Yankauer 100c includes a first end 102c configured for suctioning blood or related matter, a tubular straw 104c extending from end 102c, and a second end 106c on straw 104c configured to telescopingly frictionally press-fit onto inlet 38c of valve 30c. Valve outlet 40c includes a stepped outer surface 108c such as for connecting to suction lines having different diameters. It is noted that casing 36c is shown as being one piece. However, it is contemplated that casing 36c could also be a multi-piece assembly such as is noted above in regard to valve 30a or as is noted below in regard to valve 30h.

Another valve 30d (FIGS. 13–15) includes first and second members 50d and 52d, respectively, that can be matably engaged to form a chamber 36d and a tortuous path-forming member 34d. An adaptor 114d is configured to matably engage the inlet 38d. Specifically, adaptor 114d includes a ring 116d having a diameter chosen so that it frictionally sealingly engages inlet 38d, and an abutting lip 118d for engaging the end of inlet 38d to prevent overtravel of adaptor 114d into inlet 38d. Adaptor 114d further defines a second inlet 38d' having a reduced size compared to inlet 38d so that, for example, an ejector 76d can be attached to second inlet 38d'. A frustoconically shaped wall 120d interconnects ring 116d and second inlet 38d'. FIG. 16 illustrates use of valve 30d without adaptor 114d, valve 30d being connected to an evacuator 90d.

It is contemplated that some applications may require an even more tortuous path than tortuous paths 42 of valve 30 shown in FIG. 5 and valves 30a through 30d shown in FIGS. 6–16. For this purpose, a valve 30e including a separate insert 124e (FIG. 17) is provided. Insert 124e is shaped generally similarly to second member 52, but insert 124e does not include a frustoconically shaped section 62. Rather, second insert 124e is configured to fit within and frictionally engage the inside surfaces of casing 32e. More specifically, insert 124e includes tubular protruding section 68e and ring-shaped fin 72e. A circumferential rib 125e on tubular protruding section 68e extends outwardly and is configured to engage a depression 126e in cylindrically shaped wall 56e of casing 32e. It is noted that depression 126e can be located anywhere in casing 32e, and that multiple depressions 126e can be used to locate multiple inserts 124e in casing 32e. Tubular protruding section 68e further includes an end 127e configured to engage the inside surface on the end of frustoconically shaped section 62e. Casing 32e is constructed of opposing members such as members 50e and 52e due to the large diameter of ring-shaped fin 72e. Notably, more than one insert 124e can be positioned in casing 32e at a time, thus greatly increasing the effective length of the tortuous path.

Another insert 129f (FIG. 18) is identical to insert 124e except that insert 129f includes a second ring-shaped fin 72f spaced longitudinally apart from first ring-shaped fin 72f on tubular protruding section 68f. Also, end 127f is formed with orthogonal surfaces. It is contemplated that even more than two fins 72f could be located on insert 129f, or that multiple inserts 124e and/or 129f could be positioned inside of casing (32e).

FIGS. 19 and 20 show a valve 30g including members 50g and 52g, and an insert 124g in combination with an evacuator 90g. Valve 30g includes a pair of reversely lipped ring-shaped fins 72g and 72g', fin 72g being on member 52g and fin 72g' being on insert 124g. Insert 124g further includes cylindrically shaped end 127g configured to securely frictionally engage the inside of casing 32g. Notably, a double-finned insert as illustrated by insert 129f can be substituted for insert 124g, in which case the valve 30g would define three ring-shaped fins.

Figure 21:
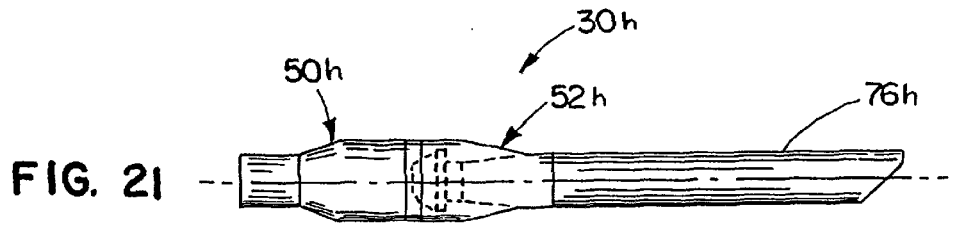
FIG. 21 is a side view of a ninth embodiment valve connected to a disposal oral evacuator.
Figure 22:
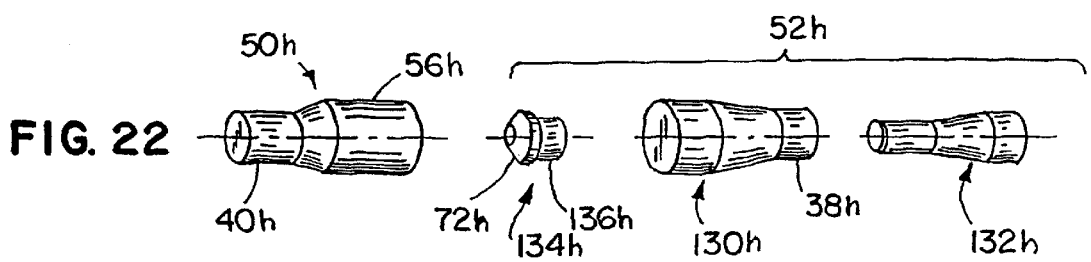
FIG. 22 is an exploded perspective view of the assembly shown in FIG. 21.
Figure 23:
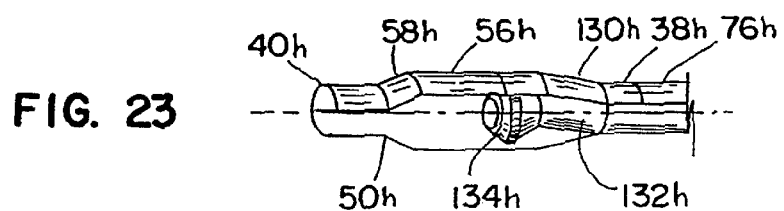
FIG. 23 is a perspective view of the valve shown in FIG. 21 with the housing partially broken away to illustrate the interior of the valve.

In FIGS. 21–23, a valve 30h is illustrated that includes members 50h and 52h. Member 52h is three piece and includes a chamber-forming shell 130h, a tubular protruding section 132h and a ring-shaped member 134h configured to matably engage tubular protruding section 132h. Ring-shaped member 134h includes a ring-shaped fin 72h and a tubular end or stub 136h configured to frictionally engage the end of tubular protruding section 132h. Notably, it is contemplated that tubular protruding section 132h can be an integral part of another member such as an ejector 76h. To assemble member 52h, the tubular protruding section 132h is press-fittingly sealingly extended through inlet 38h of casing 32h, and tubular stub 136h on ring-shaped member 134h is frictionally engaged onto tubular protruding section 132h. Valve 30h is then assembled by press-fittingly or otherwise assembling members 50h and 52h together.

Figure 24:
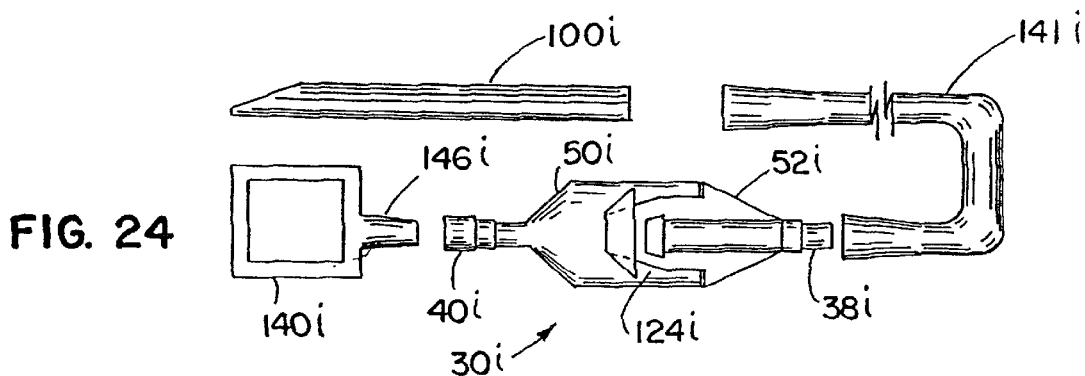
FIG. 24 is a side view of a tenth embodiment valve connected at one end to a disposable connecting tube and yankauer and at the other end to a medical suctioning unit.
Figure 25:
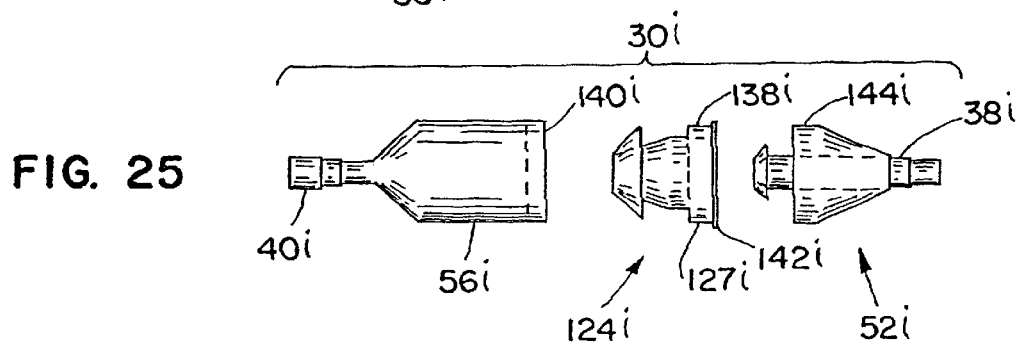
FIG. 25 is an exploded side view of the valve shown in FIG. 24.

In FIGS. 24–25, a valve 30i generally comparable to valve 30g is attached to medical suction unit 140i at outlet 40i and to a yankauer 100i by a disposable flexible tube or hose 141i. Valve 30i includes an insert 124i having an end 127i with a cylindrically shaped outer surface 138i for engaging a recess 140i in cylindrically shaped wall 56i. A radially extending surface 142i limits insertion of insert 124i into cylindrically shaped wall 56i. Member 52i includes a cylindrically shaped wall 144i sized to telescopingly slide over insert surface 142i and frictionally securely engage the outer surface of cylindrically shaped wall 56i. Valve member 52i includes an inlet 38i configured to receive flexible tube 141i, and valve member 50i includes a stepped outlet 40i configured to receive a connector 146i on medical suction unit 140i.

An eleventh embodiment, and currently the preferred embodiment, is illustrated in FIGS. 26–27 and designated 30j. This embodiment of the valve includes a housing 50j, an inlet insert 52j, and a diffuser 150j. The unique component of this embodiment is the diffuser 150j; the housing 50j and inlet insert 52j can be any of the constructions described above.

The housing 50j includes an outlet stem 40j, a frustoconical peripheral wall 56j, and a frustoconical neck 58j interconnecting the foregoing. These three portions are axially aligned with one another and are fabricated as a single piece.

The inlet insert 52j includes an inlet stem 38j, a shoulder 62j, and a tubular extension 68j. These three portion are axially aligned with one another and are fabricated as a single piece. The shoulder 62j is configured to friction fit or snap fit into the housing 50j. The inlet extension extends into the chamber 36j and terminates in an inlet mouth 71j. A peripheral circumferential rib 72j on the extension 68j surrounds the inlet mouth 71j.

The tortuous surface path, as in the other devices includes a) the entire interior surface of the housing 50j, b) the interior surface of the shoulder 62j, c) the exterior surface of the inlet extension 68j, and the rib 72j. The reverse created by the inlet extension 68j and the sharp edge of the rib 72j are particularly effective in contributing to the tortuous path.

The diffuser 150j includes a central portion 152j and a peripheral portion surrounding the central portion. The diffuser is shown in two positions in FIG. 27—a plan view and a side view illustrating the diffuser for insertion into the housing 50j. The central portion is unapertured. The peripheral portion is, in essence, apertured by scallops 154j leaving arms 156j. The diffuser is press-fitted or snap-fitted within the housing 50j proximate the outlet stem 40j and the neck 58j. The arms 156j engage the peripheral wall 56j.

The diameter of the diffuser central portion 152j is larger than the interior diameter of the outlet stem 40j and larger than the diameter of the inlet mouth 71j. Consequently, the diffuser 150j blocks all direct lines or paths between the outlet 40j and the inlet 38j. This prevents backflowing fluid from traveling directly through the chamber from the outlet to the inlet. Another way of stating the size relationship is that the cross-sectional area of the central portion is larger than the cross-sectional area of the outlet 40j and is larger than the cross-sectional area of the inlet 38j.

Further, the diffuser 150j directs all backflowing fluid from the outlet 40j to the peripheral wall 56j. This ensures that all backflowing fluids and any bacteria or other contaminants therein will be forced to follow the full length of the tortuous path. This even further reduces the likelihood that any bacteria will traverse the full length of the tortuous path and enter the inlet 38j;

The above descriptions are those of preferred embodiments of the invention. Various alterations and changes can be made without departing from the spirit and broader aspects of the invention as defined in the claims, which are to be interpreted in accordance with the principles of patent law including the doctrine of equivalents.

The embodiments of the invention in which an exclusive property or privilege is claimed are defined as follows:

1. A medical suctioning method comprising:

drawing a vacuum in a line;

inserting a valve into the line, the valve being closed with the exception of an inlet and an outlet, said inlet formed at an end of a tubular extension extending into the valve, said inlet surrounded by a continuous circumferential rib on and extending radially outward from the tubular extension; and providing a tortuous surface path through the valve between the inlet and the outlet, the tortuous path comprising the tubular extension and the circumferential rib, whereby backflow of body fluids and bacteria through the valve is prevented.

2. A medical suctioning method as defined in claim 1 wherein the valve has a peripheral wall and wherein said method further comprises diffusing fluid backflowing through the outlet toward the peripheral wall.

3. A medical suctioning method as defined in cliam 2 wherein said diffusing step includes diffusing all of the liquid that otherwise might backflow in a direct line from the outlet to the inlet.

4. A method of suctioning fluids from a body comprising:

connecting a first line to an inlet of a backflow valve, the backflow valve including a peripheral wall, said inlet formed at an end of a tubular extension extending into the valve, said inlet surrounded by a continuous circumferential rib on and extending radially outward from the tubular extension;

connecting a second line to an outlet of the backflow valve;

drawing a vacuum on the second line, thereby drawing a vacuum through the valve and the first line; and providing a tortuous surface path between the inlet and the outlet, the tortuous path comprising the tubular extension and the circumferential rib, whereby backflow of body fluids and bacteria through the valve is prevented; and diffusing fluid backflowing through the outlet radially outwardly toward the peripheral wall.

5. A method as defined in claim 4 wherein said diffusing step comprises diffusing all of the liquid that might otherwise backflow in a direct line from the outlet to the inlet.

6. A method as defined in claim 4 wherein said providing step includes forming the inlet at the end of a tubular extension extending into the valve.

7. A method as defined in claim 6 wherein said providing step further includes forming a circumferential rib on the tubular extension about the inlet.

* * * * *